United States Patent
Seki et al.

(10) Patent No.: US 10,588,548 B2
(45) Date of Patent: Mar. 17, 2020

(54) CHEWING DETECTING DEVICE

(71) Applicants: LOTTE CO., LTD., Tokyo (JP);
DENTSU INC., Tokyo (JP)

(72) Inventors: Tetsuya Seki, Tokyo (JP); Shusaku Hirota, Tokyo (JP); Yusuke Chishiro, Tokyo (JP)

(73) Assignees: LOTTE CO., LTD., Tokyo (JP); DENTSU INC., Tokyo (JP)

( * ) Notice: Subject to any disclaimer, the term of this patent is extended or adjusted under 35 U.S.C. 154(b) by 413 days.

(21) Appl. No.: 15/520,672

(22) PCT Filed: Oct. 19, 2015

(86) PCT No.: PCT/JP2015/079481
§ 371 (c)(1),
(2) Date: Apr. 20, 2017

(87) PCT Pub. No.: WO2016/063844
PCT Pub. Date: Apr. 28, 2016

(65) Prior Publication Data
US 2017/0303828 A1    Oct. 26, 2017

(30) Foreign Application Priority Data
Oct. 20, 2014  (JP) .................................. 2014-214012

(51) Int. Cl.
*A61B 5/11* (2006.01)
*A61B 5/00* (2006.01)

(52) U.S. Cl.
CPC .......... *A61B 5/1126* (2013.01); *A61B 5/0082* (2013.01); *A61B 5/6803* (2013.01);
(Continued)

(58) Field of Classification Search
CPC ... A61B 5/0082; A61B 5/1126; A61B 5/6817; A61B 5/7271; A61B 5/7214; A61B 5/6803
See application file for complete search history.

(56) References Cited

U.S. PATENT DOCUMENTS

2011/0125063 A1 * 5/2011 Shalon ................. A61B 5/0006
600/590
2012/0001846 A1 1/2012 Taniguchi et al.
(Continued)

FOREIGN PATENT DOCUMENTS

CN        102670206 A    9/2012
EP        2716212 A1     4/2014
(Continued)

*Primary Examiner* — Bo Joseph Peng
(74) *Attorney, Agent, or Firm* — Rabin & Berdo, P.C.

(57) ABSTRACT

A chewing detecting device includes: earphone-type external auditory meatus sensors which have a pair of a light emitting element and a light receiving element and in which the light receiving element receives reflective light of light emitted by the light emitting element into an external auditory meatus to output a voltage signal corresponding to a light receiving amount; association processing means associating an output signal of the external auditory meatus sensors with a motion of a jaw, and outputting a chewing signal showing that the jaw performs chewing; and chewing section sensing means which determines whether or not an output of the external auditory meatus sensors is based on the motion of the jaw (within a chewing section), and which invalidates the output of the association processing means when the output of the external auditory meatus sensors is not based on the motion of the jaw (without the chewing section).

16 Claims, 6 Drawing Sheets

(52) U.S. Cl.
CPC .......... *A61B 5/6817* (2013.01); *A61B 5/7214* (2013.01); *A61B 5/7271* (2013.01)

(56) References Cited

U.S. PATENT DOCUMENTS

| | | |
|---|---|---|
| 2012/0238908 A1 | 9/2012 | Osako et al. |
| 2013/0010997 A1 | 1/2013 | Tanaka et al. |
| 2013/0131519 A1 | 5/2013 | LeBoeuf et al. |
| 2013/0157218 A1 | 6/2013 | Brunner et al. |
| 2015/0011898 A1* | 1/2015 | Romesburg ........ A61B 5/02416 600/479 |

FOREIGN PATENT DOCUMENTS

| | | |
|---|---|---|
| JP | S58180134 A | 10/1983 |
| JP | H07-171136 A | 7/1995 |
| JP | H07-213510 A | 8/1995 |
| JP | H11-318862 A | 11/1999 |
| JP | 2002-172103 A | 6/2002 |
| JP | 2004113315 A | 4/2004 |
| JP | 2008048791 A | 3/2008 |
| JP | 2013-013540 A | 1/2013 |
| JP | 2013-042968 A | 3/2013 |
| JP | 2014083279 A | 5/2014 |
| JP | 5543929 B2 | 7/2014 |
| JP | 3195320 U | 1/2015 |
| WO | 2012108895 A1 | 8/2012 |

* cited by examiner

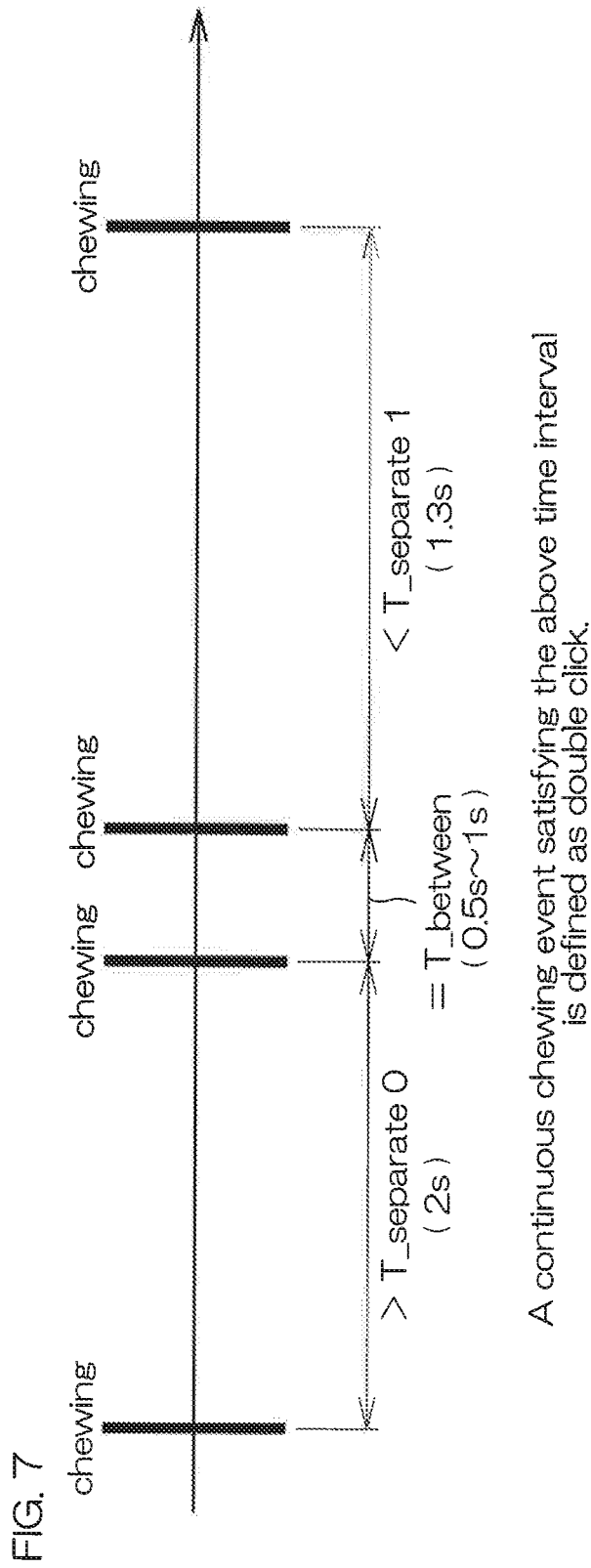

CHEWING DETECTING DEVICE

TECHNICAL FIELD

The present invention relates to a device for detecting a chewing action performed by a person.

BACKGROUND ART

A device for detecting a chewing action has been conventionally proposed.

When a person masticates a food and the like, a muscle of an external auditory meatus moves along with a move of a jaw. A device disclosed in Patent Document 1 detects a pressure change in the external auditory meatus resulted from this movement of the muscle by a pressure sensor inserted in the external auditory meatus to measure the number of the pressure change as the masticating number.

While a device disclosed in Patent Document 2 measures the masticating number using a similar principle, it describes that a low pressure sensor, a piezoelectric sensor and a press sensor are used as pressure sensors.

While an input device proposed in Patent Document 3 recognizes a state of a countenance, it is described that the input device can also detect a chewing action based on an output of an optical sensor attached to an external ear.

PRIOR ART DOCUMENT

Patent Document

Patent document 1: Japanese Unexamined Patent Publication No. H07-213510
Patent document 2: Japanese Unexamined Patent Publication No. H11-318862
Patent document 3: Japanese Patent No. 5543929

SUMMARY OF THE INVENTION

Subject to be Solved by the Invention

The conventionally proposed devices for detecting chewing respectively have the following problems.

Since the devices described in Patent documents 1 and 2 use a pressure sensor for detecting a movement of an external auditory meatus, the sensor grows in size and needs to be attached airtightly, and this makes it difficult to attach the devices for a long time.

On the other hand, while the sensor of the device proposed in Patent document 3 is an optical sensor and does not have the problems of the devices proposed in Patent documents 1 and 2, there is a problem that since a signal obtained by an optical sensor contains many noises, a chewing action cannot be precisely detected.

This invention has been made to solve such problems that conventional devices have, and a main purpose thereof is to provide a chewing detecting device that can be worn for a long time and can precisely detect a chewing.

Solution to Problem

An invention according to claim 1 is a device for detecting a chewing action performed by a person, the chewing detecting device including: an earphone-type external auditory meatus sensor which has a pair of a light emitting element and a light receiving element and in which the light receiving element receives reflective light of light emitted by the light emitting element into an external auditory meatus to output a voltage signal corresponding to a light receiving amount; association processing means associating an output signal of the external auditory meatus sensor with a motion of a jaw, and outputting a chewing signal showing that the jaw performs chewing; and chewing section sensing means which determines whether or not an output of the external auditory meatus sensor is based on the motion of the jaw (within a chewing section), and which invalidates the output of the association processing means when the output of the external auditory meatus sensor is not based on the motion of the jaw (without the chewing section).

An invention according to claim 2 is a chewing detecting device according to claim 1, comprising a converter converting the output of the external auditory meatus sensor into a digital signal, wherein the converter performs signal conversion so as to output a predetermined number of sample values in a predetermined time.

An invention according to claim 3 is a chewing detecting device according to claim 2, wherein a pair of the external auditory meatus sensors, the association processing means, the chewing section sensing means and the converters are respectively provided for a left ear and a right ear.

An invention according to claim 4 is a chewing detecting device according to claim 2 or 3, wherein the chewing section sensing means has a determination sensing algorithm which determines the chewing section when a constant rate (predetermined number) or more of sample values among a constant number of sample values input from the converter within a predetermined sensing section is a significant value, and determines not the chewing section when not more than the constant rate (predetermined number) of sample values is a significant value.

An invention according to claim 5 is a chewing detecting device according to claim 4, wherein the chewing section sensing means includes: means setting a threshold value based on the smallest sample value and/or the largest sample value in the sensing section; and means determining that when a sample value exceeds the threshold value, the sample value is a significant value.

An invention according to claim 6 is a chewing detecting device according to claim 5, wherein the means setting a threshold value includes means calibrating a threshold value per user.

An invention according to claim 7 is a chewing detecting device according to any one of claims 3 to 6, further including means counting chewing and the number thereof based on a logical sum output of the association processing means to be output.

An invention according to claim 8 is a chewing detecting device according to claim 7, wherein the output means includes dead time setting means which, when a chewing signal is fed at an interval shorter than a predetermined time, excludes the chewing signal.

An invention according to claim 9 is a chewing detecting device according to claim 7 or 8, wherein the output means includes command generating means which generates a predetermined command signal and outputs it to outside when a predetermined number of continuous chewing signals are fed at a predetermined interval.

An invention according to claim 10 is a chewing detecting device according to claim 9, wherein the number of the continuous chewing signals are two.

An invention according to claim 11 is a chewing detecting device according to anyone of claims 1 to 10, wherein the external auditory meatus sensor includes: a body attached to an external auditory meatus; a pair of a light emitting element and a light receiving element disposed at a tip end of the body in a manner where air can pass between an inside and an outside of the body; a sound transmitting element disposed in the inside of the body and outputting a sound from the inside to the outside of the body; and an LED incorporated in a rear end of the body and lighting in conjunction with that the light receiving element performs a light receiving function.

Advantageous Effects of the Invention

According to this invention, there can be provided a chewing detecting device that inflicts little load while wearing, can be worn for a long time and can precisely detect a chewing while being worn.

Further, since chewing can be precisely detected, it can also be used as a device outputting various command signals based on intentional chewing. In particular, when the external auditory meatus sensor is also provided with an earphone function, an operation command can be fed to a device offering music and the like which is listened through the earphone, thereby to make a so-called hands-free operation possible.

BRIEF DESCRIPTION OF THE DRAWINGS

FIG. 7 is a view demonstrating a definition of double click.

DESCRIPTION OF EMBODIMENTS

One embodiment of this invention is described specifically below with reference to drawings.

Figure 1:
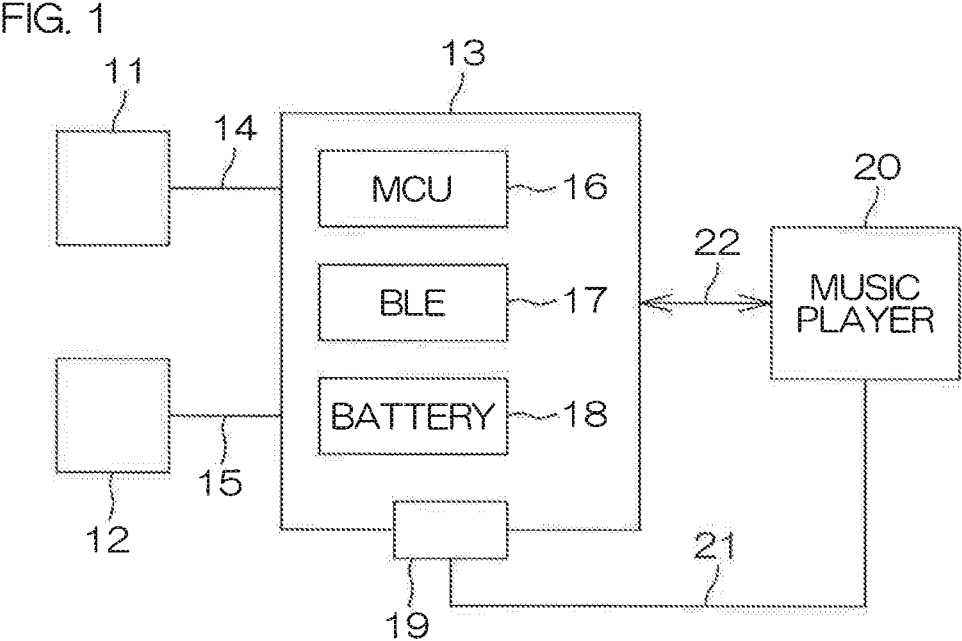
FIG. 1 is a block diagram showing a configuration of a chewing detecting device 10 according to one embodiment of the present invention.

FIG. 1 is a block diagram showing a configuration of a chewing detecting device 10 according to one embodiment of the present invention. The chewing detecting device 10 comprises an earphone-type external auditory meatus sensor (for right ear) 11, an earphone-type external auditory meatus sensor (for left ear) 12 and a body housing 13. The external auditory meatus sensors 11, 12 and the body housing 13 are connected by signal lines 14, 15.

The body housing 13 incorporates an information processing unit 16 such as an MCU (Memory Control Unit), a wireless communication unit 17 such as BLE, a battery unit 18 and a stereo jack 19.

Consequently, the chewing detecting device 10 has a relay function relaying music and the like offered from a portable music player 20 by using the stereo jack 19 and a stereo audio cable 21 to connect this portable music player 20, for example.

Further, when the portable music player 20 is one having a computer function such as a smartphone, communication through a wireless communication function (for example, Bluetooth (registered trademark)) 22 can be established between the body housing 13 and the portable music player 20.

Figure 2:
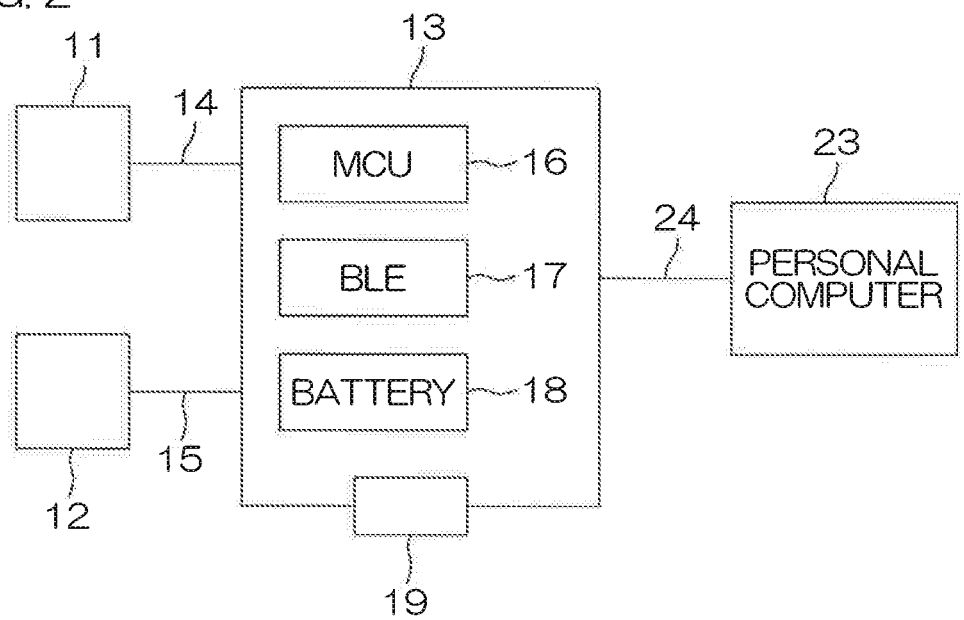
FIG. 2 is a block diagram showing a configuration of a chewing detecting device 10 according to one embodiment of the present invention.

Further, as shown in FIG. 2, the chewing detecting device 10 is provided with a connector (not shown) (for example, micro USB terminal) in the body housing 13 and can connect an external personal computer 23 via a signal cable 24.

As shown in FIGS. 1 and 2, in this embodiment, the configuration where the body housing 13 and the external auditory meatus sensors 11, 12 are respectively connected by the signal lines 14, 15 is shown. However, it is also possible that the signal lines 14, 15 are omitted and the body housing 13 and the external auditory meatus sensors 11, 12 are connected by wireless communication.

Figure 3:
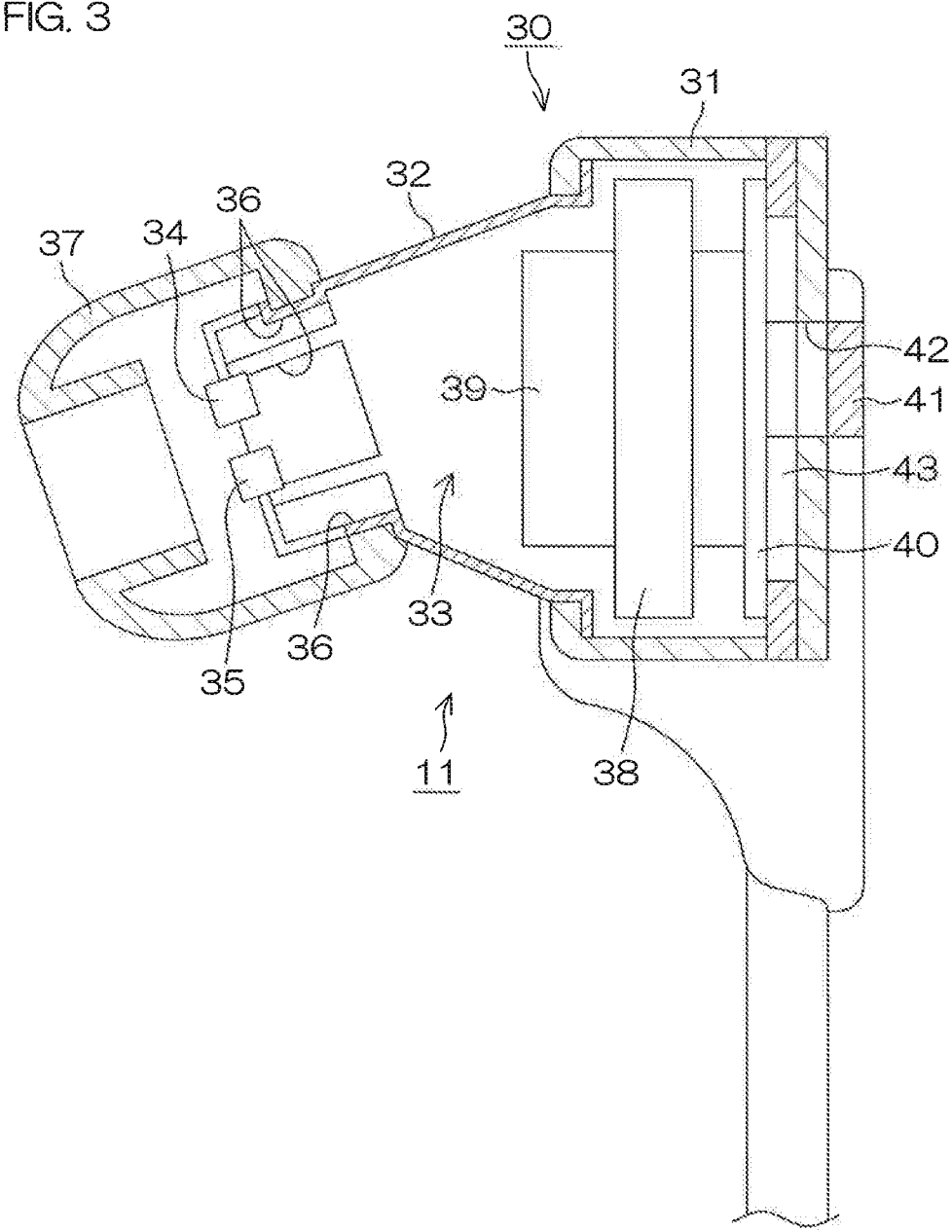
FIG. 3 is an illustrative view for illustrating a configuration of an external auditory meatus sensor 11.

FIG. 3 is an illustrative view for illustrating a configuration of the external auditory meatus sensor 11. Here, while a configuration of the external auditory meatus sensor 11 is described as an example, a configuration of the external auditory meatus sensor 12 is identical.

The external auditory meatus sensor 11 has a body 30 which is attached to an external auditory meatus. The body 30 has a base portion 31 and a projecting portion 32 projecting in a tapered manner tapering forward from the base portion 31, and an inside thereof is a space 33. A tip end of the projecting portion 32 is provided with a pair of a light emitting element 34 and a light receiving element 35. The light emitting element 34 is configured of an infrared light emitting diode, for example.

The light receiving element 35 is configured of a phototransistor, for example. Light emitted by the light emitting element 34 is reflected on the external auditory meatus, and in order that the light receiving element 35 can receive this reflected light, the light emitting element 34 and the light receiving element 35 are arranged such that they are close and have predetermined positional and angular relations to each other.

On a side of the tip end of the projecting portion 32, a window 36 is opened so that air in the space 33 can pass to a front outside.

Further, on the tip end of the projecting portion 32, the window 36, the light emitting element 34 and the light receiving element 35 are covered by an ear pad 37 formed of an elastic material.

In the space 33 of the body 30, a circuit board 38 and a compact speaker 39 installed on the circuit board 38 are provided with an inside of the base portion 31 centered. The compact speaker 39 functions an sound transmitting element and can output music and the like.

An LED 41 installed on a substrate 40 is incorporated in the base portion 31 on a rear end side thereof. An upper end of the LED 41 faces outward from a hole 42 formed in a rear end surface of the base portion 31. Thus, light emission of the LED 41 can be observed visually from an outside (rear side) of the body 30. Further, a disk-shaped light guide plate 43 is incorporated to the base portion 31 so as to surround a periphery of the LED 41. Thus, lighting of the LED 41 can be observed visually through the light guide plate 43 also from a side of a side surface of the body 30.

In this example, the LED 41 provided in the external auditory meatus sensor 11 is configured to light on in conjunction with that the light receiving element 35 performs a light receiving function.

Figure 4:
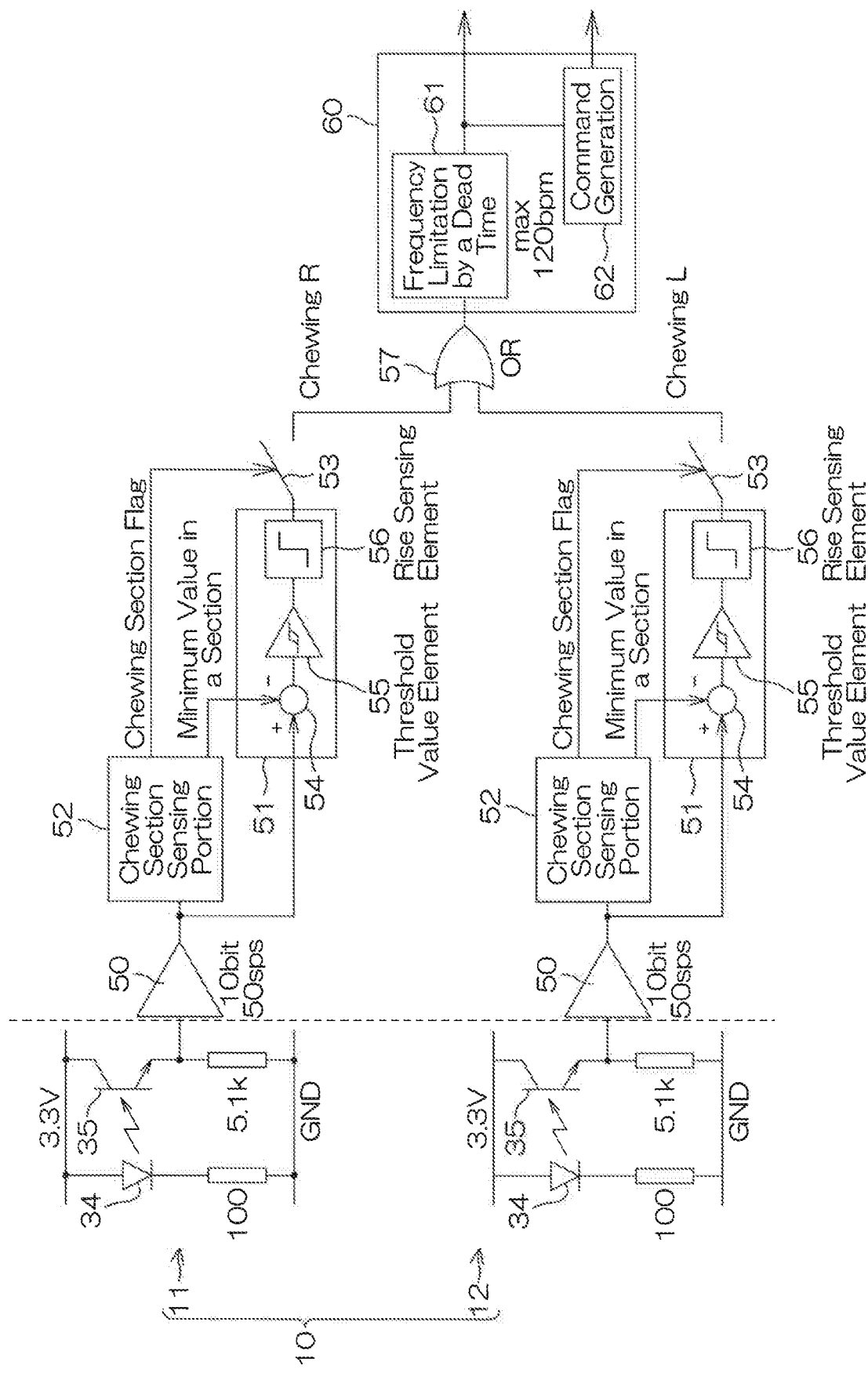
FIG. 4 is a circuit block diagram showing a configurational example of a chewing detecting device 10 according to this embodiment.

FIG. 4 is a circuit block diagram showing a configurational example of the chewing detecting device 10 according to this embodiment.

Referring to FIG. 4, the chewing detecting device 10 has the external auditory meatus sensor (for right ear) 11 and the external auditory meatus sensor (for left ear) 12. A pair of these external auditory meatus sensors 11, 12 have the light emitting element 34 and the light receiving element 35 respectively. Light emitted by the light emitting element 34 is reflected in the external auditory meatus, and the light receiving element 35 receives this reflected light to output a voltage signal corresponding to a light receiving amount.

The voltage signal to be output is an analog signal and is fed to a converter 50. The converter converts an input analog voltage signal into a digital signal of, for example, 10 bits. A conversion capacity of the converter is set to, for example, 50 samples/second. Consequently, the converter 50 outputs 50 sample values per second.

The outputs of the converter 50 are parallelly fed to an association processing portion 51 and the chewing section sensing portion 52. The association processing portion 51 associates the outputs of the converter 50 with a motion of a jaw, and outputs a chewing signal (for example, a pulse signal) showing that the jaw performs chewing.

On the other hand, the chewing section sensing portion 52 is a processing portion which determines whether or not the outputs of the converter 50 are based on a motion of a jaw (within a chewing section), and which invalidates the chewing signal output from the association processing portion 51 when the outputs of the converter 50 are not based on the motion of the jaw (without the chewing section). In the circuit block diagram of FIG. 4, the chewing section sensing portion 52 has a configuration of operating a switch 53. When the switch 53 is not closed, the chewing signal of the association processing portion 51 is not sent to a later stage, and the output (chewing signal) is invalidated.

Next, a specific description is made with respect to a manner of determination whether it is within or without the chewing section performed in the chewing section sensing portion 52.

Figure 5:
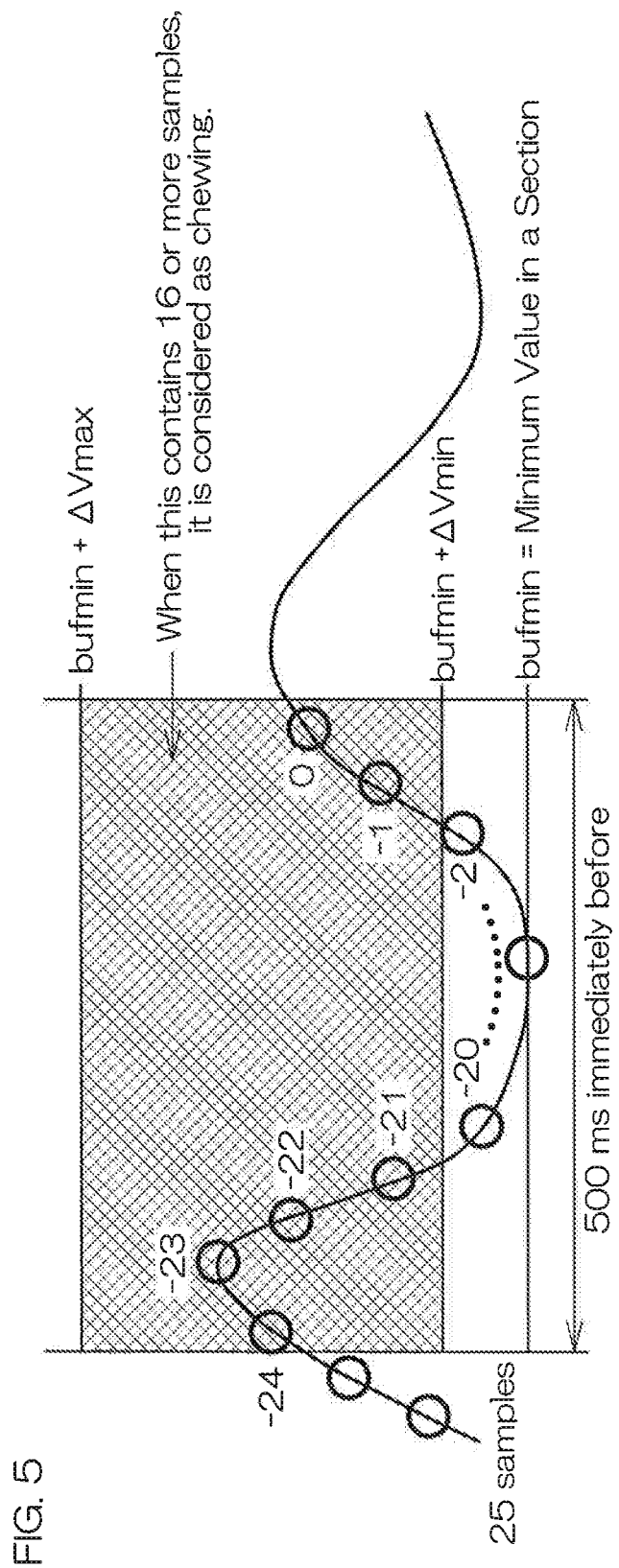
FIG. 5 is a view illustrating a sensing algorithm performed at a chewing section sensing portion 52.

FIG. 5 is a view illustrating a sensing algorithm performed in the chewing section sensing portion 52. Based on 25 continuous sample values fed from the converter 50, the chewing section sensing portion 52 determines whether or not a sample value next fed is a sample value based on a motion of a jaw, that is, a sample value within the chewing section.

Specifically, 25 sample values are input from the converter 50 to the chewing section sensing portion 52 during 0.5 second. Then it is examined how many sample values of the 25 sample values are present within a range where a minimum value bufmin in these 25 sample values is added with a predetermined lower limit value ΔVmin and a predetermined upper limit value ΔVmax. When the number of sample values within this range is 16 or more (64% or more), it is determined that a sample value next fed from the converter 50 is a sample value based on a motion of a jaw, that is, a sample value within the chewing section.

On the other hand, when only less than 16 sample values of the 25 continuous sample values input during 0.5 second are within the above range, a sample value subsequently input is determined as a sample value which is not based on a motion of a jaw, that is, which is detected without the chewing section, and invalidation processing (processing of opening the switch 53 in FIG. 4) is performed at this timing.

Thus, in this embodiment, the chewing section sensing portion 52 has employed a sensing algorithm which determines whether or not a sample value output from the converter 50 is a sample value within the chewing section based on a value of the 25 sample values fed during 500 milliseconds immediately before this sample value is output.

Since such an algorithm is employed, outputs of the external auditory meatus sensors 11, 12 containing much noise can be favorably filtered, and a signal (sample value) resulted from actual chewing can be correctly extracted, whereby precise chewing detection can be performed.

More specifically, sample values obtained from the external auditory meatus sensors 11, 12 when a user wearing this chewing detecting device 10 walks and moves the head, for example, but does not do a chewing action, or sample values of the external auditory meatus sensors 11, 12 sensed when a user sings or talks, for example, but does not do chewing can be appropriately determined as sample values without the chewing section, whereby only a sample value within the chewing section can be favorably extracted. Therefore, a device that is practical and without malfunction can be achieved.

Additionally, sensing of the chewing section is not limited to one performed based on 0.5 second period but may be performed by setting any unit time and based on that unit time.

In the illustrative view of the sensing algorithm of FIG. 5, it is effective for performing a more precise chewing section detection that the lower limit value ΔVmin and the upper limit value ΔVmax of a valid range can be calibrated per user.

Figure 6:
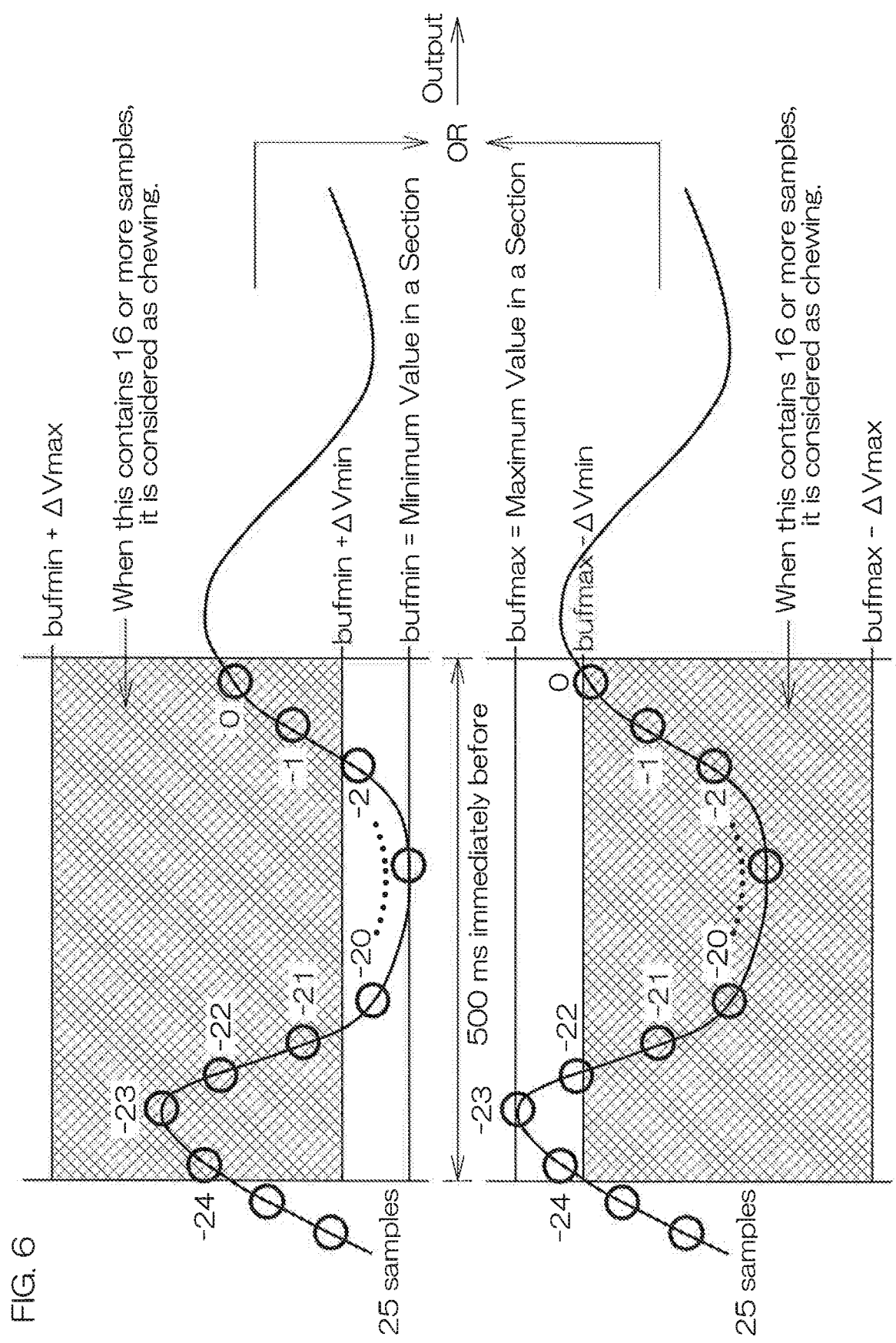
FIG. 6 is a view showing other example of a sensing algorithm performed at the chewing section sensing portion 52.

FIG. 6 is a view showing other example of a sensing algorithm performed in the chewing section sensing portion 52. As shown in FIG. 5, a change waveform of the sample value output from the converter 50 is not always lower but may be a raised change waveform.

Therefore, one where the lower limit value ΔVmin and the upper limit value ΔVmax are set based on the minimum value bufmin in a section for sensing (500 milliseconds immediately before) and one where the lower limit value ΔVmin and the upper limit value ΔVmax are set based on a maximum value bufmax in the section may be set to use a logical sum of outputs obtained by these sensing algorithms as a chewing section sensing determination output.

Referring again to FIG. 4, a configuration and operation of the association processing portion 51 are described. As described above, the association processing portion 51 is a circuit that associates the output signal of the external auditory meatus sensor 11 (or the external auditory meatus sensor 12) with a motion of a jaw and outputs the chewing signal showing that the jaw performs chewing. In this example, the association processing portion 51 is realized by an adder 54, a threshold value element 55 and a rise sensing element 56. The adder 54 subtracts (minus-adds) a minimum value in a section fed from the chewing section sensing portion 52 from the sample value output from the converter 50. Then a sample value after addition is compared to a predetermined threshold value in the threshold value element 55 to be converted to a binary datum of 0 or 1. The rise sensing element 56 senses a timing where the binary datum output from the threshold value element 55 changes from 0 to 1, that is, a rise timing to make an output.

These processes performed in the association processing portion 51 are processes of detecting a change point from a valley to a peak of a waveform presented by continuous sample values obtained related to a motion of a jaw, in a manner of speaking, to output the chewing signal.

The signal detected by the external auditory meatus sensor (for left ear) 12 is also processed in a similar manner.

The chewing signals from both circuits are fed to an output portion 60 via an OR gate 57.

In this embodiment, the output portion 60 is provided with a frequency limiting portion 61 by a dead time. The frequency limiting portion 61 functions as dead time setting means, and when a chewing signal is fed at an interval shorter than a predetermined time, for example, shorter than 0.5 second, the frequency limiting portion 61 serves to exclude the chewing signal with such a short time interval.

In this embodiment, chewing is detected based on the outputs of both the right and left external auditory meatus sensors 11, 12. However, it has been confirmed experimentally that left and right signals may be output in an unsynchronized manner depending on individuals, and that chewing signals may be output at the number more than an actual chewing number. Therefore, the frequency limiting portion 61 by a dead time is provided to prevent erroneous sensing, whereby the number of chewing can be more correctly detected.

Additionally, it is also possible to employ a configuration where the frequency limiting portion 61 by a dead time is omitted.

The output portion 60 may be further provided with a command generating portion 62. The command generating portion 62 is a circuit which, for example, detects the plural number of chewing of a predetermined time interval performed by a user intently and generates a specific command signal based on this plural number of chewing detection.

FIG. 7 is a view demonstrating a definition of double click. As shown in FIG. 7, two chewing performed at a time interval of 0.5 to 1 second is defined as double click. When this double click is detected, the command generating portion 62 can be configured to generate a predetermined command signal based on the double click and output this to an external apparatus and the like. This command signal is a start signal, a stop signal and the like of the portable music player 20 when the portable music player 20 is used as shown in FIG. 1, for example.

The command generating portion 62 may generate a predetermined operation command signal when detecting triple click (three chewing performed continuously at a predetermined interval), for example, other than when detecting the above double click.

Since the chewing detecting device 10 according to this embodiment has the above-described configuration, a wearing load at a time of wearing the external auditory meatus sensors 11, 12 is low and wearing for a long time is possible.

Further, it is possible that detection signals obtained from these external auditory meatus sensors 11, 12 can be properly filtered to significantly precisely detect chewing actions and the number thereof.

This invention does not limited to the above-described embodiments, and various modifications are possible within the scope of the claims. Further, since chewing and the number thereof obtained through this embodiment are correctly detected, they can be widely used in various applications.

INDUSTRIAL APPLICABILITY

Since a widely practical and applicable chewing detecting device capable of performing correct chewing detection can be provided, industrial applicability is high.

LIST OF REFERENCE NUMERALS 10 chewing detecting device
11, 12 external auditory meatus sensors
13 body housing
14, 15 signal lines
16 information processing unit
17 wireless communication unit
18 battery unit
19 stereo jack
20 portable music player
21 stereo audio cable
22 wireless communication function
23 personal computer
24 signal cable
30 body
31 base portion
32 projecting portion
33 space
34 light emitting element
35 light receiving element
36 window
37 ear pad
38 circuit board
39 speaker
40 substrate
41 LED
42 hole
43 light guide plate
50 converter
51 association processing portion
52 chewing section sensing portion
53 switch
54 adder
55 threshold value element
56 rise sensing element
57 OR gate
60 output portion
61 frequency limiting portion
62 command generating portion

The invention claimed is:

1. A device for detecting a chewing action performed by a person, the chewing detecting device including:
   an earphone-type external auditory meatus sensor which has a pair of a light emitting element and a light receiving element and in which the light receiving element receives reflective light of light emitted by the light emitting element into an external auditory meatus to output a voltage signal corresponding to a light receiving amount;
   an association processing circuit configured to associate an output signal of the external auditory meatus sensor with a motion of a jaw, and output chewing signal showing that the jaw performs chewing; and
   a chewing section sensing circuit configured to determine whether or not an output of the external auditory meatus sensor is based on the motion of the jaw within a chewing section, and invalidate the output of the association processing circuit when the output of the external auditory meatus sensor is not based on the motion of the jaw without the chewing section.

2. The chewing detecting device according to claim 1, comprising a converter converting the output of the external auditory meatus sensor into a digital signal, wherein
   the converter performs signal conversion so as to output a predetermined number of sample values in a predetermined time.

3. The chewing detecting device according to claim 2, wherein a pair of the external auditory meatus sensors, the association processing circuit, the chewing section sensing circuit and the converters are respectively provided for a left ear and a right ear.

4. The chewing detecting device according to claim 3, wherein the chewing section sensing circuit determines the chewing section when at least a first predetermined number of samples that each have a significant value is included among a second predetermined number of samples, and determines a non-chewing section when not more than the first predetermined number of samples that each have the significant value is included among the second predetermined number of samples, the second predetermined samples being input from the converter within a predetermined section.

5. The chewing detecting device according to claim 3, further including an output circuit configured to count a number of the chewing action based on a logical sum output of the association processing circuit to be output.

6. The chewing detecting device according to claim 2, wherein the chewing section sensing circuit determines the chewing section when at least a first predetermined number of samples that each have a significant value is included among a second predetermined number of samples, and determines a non-chewing section when not more than the first predetermined number of samples that each have the significant value is included among the second predetermined number of samples, the second predetermined samples being input from the converter within a predetermined section.

7. The chewing detecting device according to claim 6, wherein the chewing section sensing circuit includes:
 a circuit configured to set a threshold value based on the smallest sample value and/or the largest sample value in the sensing section; and
 a circuit configured to determine that when a sample value exceeds the threshold value, the sample value is the significant value.

8. The chewing detecting device according to claim 6, further including an output circuit configured to count a number of the chewing action based on a logical sum output of the association processing circuit to be output.

9. The chewing detecting device according to claim 7, wherein the circuit configured to set the threshold value includes a circuit configured to calibrate the threshold value per user.

10. The chewing detecting device according to claim 7, further including an output circuit configured to count a number of the chewing action based on a logical sum output of the association processing circuit to be output.

11. The chewing detecting device according claim 9, further including an output circuit configured to count a number of the chewing action based on a logical sum output of the association processing circuit to be output.

12. The chewing detecting device according to claim 11, wherein the output circuit includes a dead time setting circuit which, when the chewing signal is fed at an interval shorter than a predetermined time, excludes the chewing signal.

13. The chewing detecting device according to claim 11, wherein the output circuit includes a command generating circuit which generates a predetermined command signal and outputs it to outside when a predetermined number of continuous chewing signals are fed at a predetermined interval.

14. The chewing detecting device according to claim 12, wherein the output circuit includes a command generating circuit which generates a predetermined command signal and outputs it to outside when a predetermined number of continuous chewing signals are fed at a predetermined interval.

15. The chewing detecting device according to claim 14, wherein the predetermined number of the continuous chewing signals are two.

16. The chewing detecting device according to claim 1, wherein the external auditory meatus sensor includes:
 a body attached to an external auditory meatus;
 a pair of a light emitting element and a light receiving element disposed at a tip end of the body in a manner where air can pass between an inside and an outside of the body;
 a sound transmitting element disposed in the inside of the body and outputting a sound from the inside to the outside of the body; and
 an LED incorporated in a rear end of the body and lighting in conjunction with that the light receiving element performs a light receiving function.

* * * * *